US011564927B2

(12) United States Patent
Pachter et al.

(10) Patent No.: US 11,564,927 B2
(45) Date of Patent: *Jan. 31, 2023

(54) THERAPEUTIC COMPOSITIONS, COMBINATIONS, AND METHODS OF USE

(71) Applicant: Verastem, Inc., Needham, MA (US)

(72) Inventors: Jonathan A. Pachter, Wayland, MA (US); Jennifer E. Ring, Needham, MA (US); David T. Weaver, Needham, MA (US); Yan Wang, Needham, MA (US)

(73) Assignee: Verastem, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,384

(22) Filed: Nov. 25, 2019

(65) Prior Publication Data
US 2020/0330471 A1    Oct. 22, 2020

Related U.S. Application Data

(63) Continuation of application No. 15/738,999, filed as application No. PCT/US2016/040080 on Jun. 29, 2016, now Pat. No. 10,532,056.

(60) Provisional application No. 62/186,197, filed on Jun. 29, 2015.

(51) Int. Cl.

| | | |
|---|---|---|
| *A61K 31/5377* | (2006.01) | |
| *A61K 45/06* | (2006.01) | |
| *A61K 31/506* | (2006.01) | |
| *A61K 31/7068* | (2006.01) | |
| *C07D 213/74* | (2006.01) | |
| *A61K 31/337* | (2006.01) | |
| *C07D 401/12* | (2006.01) | |
| *C07D 403/12* | (2006.01) | |
| *A61P 35/00* | (2006.01) | |
| *A61K 9/00* | (2006.01) | |
| *A61K 35/17* | (2015.01) | |
| *A61K 39/395* | (2006.01) | |
| *C07K 16/28* | (2006.01) | |
| *C07K 16/30* | (2006.01) | |

(52) U.S. Cl.
CPC ........ *A61K 31/5377* (2013.01); *A61K 9/0053* (2013.01); *A61K 31/337* (2013.01); *A61K 31/506* (2013.01); *A61K 31/7068* (2013.01); *A61K 35/17* (2013.01); *A61K 39/3955* (2013.01); *A61K 45/06* (2013.01); *A61P 35/00* (2018.01); *C07D 213/74* (2013.01); *C07D 401/12* (2013.01); *C07D 403/12* (2013.01); *C07K 16/2818* (2013.01); *C07K 16/2827* (2013.01); *C07K 16/30* (2013.01); *C07K 2317/21* (2013.01); *C07K 2317/24* (2013.01); *C07K 2319/00* (2013.01)

(58) Field of Classification Search
CPC .............. A61K 31/5377; A61K 31/337; A61K 9/0053; A61K 35/17; A61K 39/3955; A61K 45/06; A61K 31/506; A61K 31/7068; A61K 9/0019; A61K 2300/00; C07D 213/74; C07D 401/12; C07D 403/12; A61P 35/00; C07K 16/2818; C07K 16/2827; C07K 16/30; C07K 2317/21; C07K 2317/24; C07K 2319/00

See application file for complete search history.

(56) References Cited

U.S. PATENT DOCUMENTS

| | | | |
|---|---|---|---|
| 2014/0105891 A1* | 4/2014 | Garmey | ............. A61K 39/3955 |
| | | | 424/133.1 |
| 2015/0080368 A1 | 3/2015 | Luzzio et al. | |
| 2015/0118247 A1 | 4/2015 | Hotson et al. | |

FOREIGN PATENT DOCUMENTS

| | | |
|---|---|---|
| CA | 2840211 A1 | 1/2013 |
| CA | 2928908 A1 | 5/2015 |
| WO | WO-2015120289 A1 | 8/2015 |
| WO | 2017201043 A1 | 11/2017 |

OTHER PUBLICATIONS

Efficacy and safety of anti-PD-1 antibody (Nivolumab: BMS-936558, ONO-4538) in patients with platinum-resistant ovarian cancer. Junzo Hamanishi, Journal of Clinical Oncology, 32:15_suppl, 5511-5511. (Year: 2014).*

Aglietta, M. et al., "A phase I dose escalation trial of tremelimumab (CP-675,206) in combination with gemcitabine in chemotherapy-naive patients with metastatic pancreatic cancer," *Annals Of Oncology*, 2014, vol. 25, No. 9, pp. 1750-1755.

Curran, M. A. et al., "PD-1 and CTLA-4 combination blockade expands infiltrating T cells and reduces regulatory T and myeloid cells within B16 melanoma tumors", PNAS, 2010, vol. 107, No. 9, pp. 4275-4280.

Extended European search report for European Application No. 16818676.5, dated Jul. 10, 2019.

Frame, M.C. et al., "FAK to the rescue: Activated stroma promotes a "safe haven" for BRAF-mutant melanoma cells by inducing FAK signaling," Cancer Cell, 2015, 27:429-431.

Frederick, D. T. et al., "BRAF inhibition is associated with enhanced melanoma antigen expression and a more favorable tumor microenvironment in patients with metastatic melanoma," Clinical Cancer Research, 2013, vol. 19, No. 5, pp. 1225-1231.

Guha, M., "The new era of immune checkpoint inhibitors," *Pharmaceutical Journal*, Nov. 18, 2014, Retrieved from: https://www.pharmaceutical-journal.com/news-and-analysis/features/immune-checkpoint-inhibitors-bring-new-hope-to-cancer-patients/20067127.article?firstPass=false.

(Continued)

*Primary Examiner* — Sahar Javanmard
(74) *Attorney, Agent, or Firm* — Goodwin Procter LLP

(57) ABSTRACT

This invention relates to methods comprising administering a FAK inhibitor and an immunotherapeutic agent such as anti-PD-1 or anti-PD-L1; that are useful in the treatment of abnormal cell growth, such as cancer, in mammals, especially humans.

18 Claims, 6 Drawing Sheets

(56) References Cited

OTHER PUBLICATIONS

Halder, J., "Focal Adhesion Kinase Silencing Augments DocetaxelMediated Apoptosis in Ovarian Cancer Cells." *Clinical Cancer Research*, 2005, vol. 11, No. 24, pp. 8829-8836.
Hirata, E. et al., "Intravital Imaging Reveals How BRAF Inhibition Generates Drug-Tolerant Microenvironments with High Integrin [beta]1/ FAK Signaling," *Cancer Cell*, Apr. 1, 2015, vol. 27, No. 4, pp. 574-588.
International Search Report for PCT/US2016/40080 dated Sep. 7, 2016.
Kodumudi, K.N. et al., "A Novel Chemoimmunomodulating Property of Docetaxel: Suppression of Myeloid-Derived Suppressor Cells in Tumor Bearers," *Clinical Cancer Research*, 2010, vol. 16, No. 18, pp. 4583-4594.
Lazaro, G. et al., "Targeting focal adhesion kinase in ER+/ HER2+ breast cancer improves trastuzumab response," *Endocrine—Related Cancer*, 2013, vol. 20, No. 5, pp. 691-704.
Lee, B. et al., "FAK signaling in human cancer as a target for therapeutics," *Pharmacol. Ther.* Feb. 2015, vol. 146, pp. 132-149.
Linch, SN et al., "Combined OX40 ligation plus CTLA-4 blockade: More than the sum of its parts," *Oncoimmunology*, 2014, vol. 3, pp. e28245.
Mandala, M. et al., "Immunomodulating property of MAPK inhibitors: from translational knowledge to clinical implementation," The United States and Canadian Academy of Patholoy, Inc., 2016, vol. 97, No. 2, pp. 166-175.
Nuti, M. et al., "Immune Effects of Trastuzumab," *Journal of Cancer*, 2011, vol. 2, pp. 317-323.
Pachter, J. et al., "302 FAK inhibitor VS-6063 (defactinib) targets mesothelioma cancer stem cells which are enriched by standard of care chemotherapy," *Eur. J. Cancer*, 2014, vol. 50, pp. 99.
Partial supplementary search report for EP16818676 dated Feb. 15, 2019 (18 pages).
Patel, S.P. et al., "PD-L1 Expression as a Predictive Biomarker in Cancer Immunotherapy," *Mol. Cancer Ther.* Apr. 2015, vol. 14, Issue 4, pp. OF1-10.
Sagiv-Barfi, I. et al. "Therapeutic antitumor immunity by checkpoint blockade is enhanced by ibrutinib, an inhibitor of both BTK and ITK" Proc Natl Acad Sci USA, 2015, 112:9, pp. E966-E972.
Shin, D.S. et al, "The evolution of checkpoint blockade as a cancer therapy: what's here, what's next?" Curr Opin Immunol, 2015, 33, pp. 23-35.
Yoon H, et al. "Understanding the Roles of FAK in Cancer: Inhibitors, Genetic Models, and New Insights" J Histochem Cytochem, 2015, 63, 2, pp. 114-128.
Hamanishi, "Efficacy and safety of anti-PD-1 antibody (Nivolumab: BMS-936558, ONO-4538) in patients with platinum-resistant ovarian cancer". Journal of Clinical Oncology, 32:15_suppl, 5511-5511. (Year: 2014).

* cited by examiner

THERAPEUTIC COMPOSITIONS, COMBINATIONS, AND METHODS OF USE

RELATED APPLICATIONS

The present application claims the benefit under 35 U.S.C. § 120 as a continuation of U.S. application Ser. No. 15/738,999, filed on Dec. 21, 2017, which is a national stage application under 35 U.S.C. § 371 of International Application No. PCT/US2016/040080 filed Jun. 29, 2016, which claims priority under 35 U.S.C. § 119(e) to U.S. provisional patent application, U.S. Ser. No. 62/186,197 filed on Jun. 29, 2015. The entire contents of these applications are incorporated herein by reference in their entirety.

FIELD OF INVENTION

This invention relates to methods of treatment of a disease or disorder described herein (e.g., abnormal cell growth (e.g., cancer)), comprising administering to a subject (e.g., a human subject) a FAK inhibitor and an immunotherapeutic agent.

BACKGROUND OF INVENTION

Convincing evidence suggests that focal adhesion kinase (FAK), i.e., PTK2, a cytoplasmic, non-receptor tyrosine kinase, plays an essential role in cell-matrix signal transduction pathways (Clark and Bruges 1995, *Science* 268: 233-239) and its aberrant activation is associated with an increase in the metastatic potential of tumors (Owens et al. 1995, *Cancer Research* 55: 2752-2755). FAK was originally identified as a 125 kDa protein highly tyrosine-phosphorylated in cells transformed by v-Src. FAK is encoded by the PTK2 gene in humans. FAK was subsequently found to be a tyrosine kinase that localizes to focal adhesions, which are contact points between cultured cells and their underlying substratum and sites of intense tyrosine phosphorylation. FAK is phosphorylated and, thus, activated in response to extracellular matrix (ECM)-binding to integrins. Recently, studies have demonstrated that an increase in FAK mRNA levels accompanied invasive transformation of tumors and attenuation of the expression of FAK (through the use of antisense oligonucleotides) induces apoptosis in tumor cells (Xu et al. 1996, *Cell Growth and Diff.* 7: 413-418). In addition to being expressed in most tissue types, FAK is found at elevated levels in most human cancers, for example in highly invasive metastases. For example, U.S. Pat. No. 8,247,411 relates to a broad class of novel pyrimidine derivatives that are kinase inhibitors, and more specifically, inhibitors of FAK. Compounds such as these may be useful in the treatment of abnormal cell growth.

Cancers can be recognized by the immune system, and regulate and even eliminate tumors. Immune checkpoints refer to a plethora of inhibitory pathways that help maintain self-tolerance and modulate the duration and amplitude of physiological immune responses in peripheral tissues in order to minimize collateral tissue damage. Tumors co-opt certain immune-checkpoint pathways as a mechanism of immune resistance, particularly against T-cells that are specific for tumor antigens. The development of checkpoint blocking antibodies, e.g., inhibitory receptors, that target or are directed against, e.g., cytotoxic T-lymphocyte antigen 4 (CTLA-4) and programmed death 1 receptor (PD-1), can facilitate the treatment of a disease or disorder described herein (e.g., abnormal cell growth, e.g., cancer (e.g., a cancer described herein)). CTLA-4 and PD-1 can function as negative regulators and have non-redundant roles in modulating immune responses. They are expressed on tumor-specific T-cells and can lead to compromised activation and suppressed effector functions e.g., profileration, cytokine secretion, and tumor cell lysis. CTLA-4 can attenuate the early activation of naïve and memory T-cells. PD-1 is involved in modulating T-cell activity in e.g., peripheral tissues, e.g., via interaction with its ligands, i.e., PD-L1 and PD-L2. Blockers of the immune checkpoint pathway (e.g. anti-PD-1, anti-PD-L1, anti-CTLA-4,) can enhance antitumor immunity and provide opportunities to treat a disease or disorder described herein (e.g., abnormal cell growth, e.g., cancer (e.g., a cancer described herein)), e.g., provide more effective treatment for subjects suffering from cancer.

Although durable responses to single agent immune checkpoint inhibitors have been reported, additional approaches are needed to extend this therapeutic benefit to a greater proportion of cancer patients. Accordingly, substantial efforts are ongoing to identify agents that can augment T-cell mediated killing of tumor cells and potentiate the effects of checkpoint inhibitors. Focal Adhesion Kinase (FAK) and the closely related family member PYK2 are potentially valuable targets in this regard due to the roles of these enzymes in regulating key cellular populations in the tumor microenvironment. FAK inhibitors may increase cytotoxic T-cells (CD8+ expressing cytotoxic T-cells) in tumors, and decrease the immune cell populations that suppress the host anti-tumor immune response (T-regs, M2 tumor associated macrophages, myeloid-derived suppressor cells). FAK inhibitors can turn up the PD-1/PD-L1 immune checkpoint pathway and may augment anti-tumor efficacy of various anti-tumor immunotherapies. A combination of a cancer therapy (e.g., a FAK inhibitor) with a cancer immunotherapy (e.g. anti-PD-1, anti-PD-L1, anti-CTLA-4), may enhance the generation and effectiveness of tumor-specific cytotoxic lymphocytes and provide a promising approach for more effectively treating a disease or disorder described herein (e.g., abnormal cell growth, e.g., cancer (e.g., a cancer described herein)). The compounds described herein, e.g., FAK inhibitors, may be used in combination with an immunotherapy described herein, to prevent and treat a disease or disorder described herein, e.g., abnormal cell growth (e.g., a cancer described herein).

SUMMARY OF THE INVENTION

In an aspect, described herein is a method for treating a human subject suffering from a disease or disorder described herein (e.g., abnormal cell growth, e.g., cancer (e.g., a cancer described herein)), comprising administering a FAK inhibitor in combination with an immunotherapeutic agent or procedure (e.g., wherein the immunotherapeutic agent is a compound that inhibits the immune checkpoint blockade pathway).

In some embodiments, the cancer is a solid tumor, soft tissue tumor, metastasis, or non-solid cancer. In some embodiments, the cancer is solid tumor. In some embodiments, the solid tumor is a malignancy (e.g., sarcomas, adenocarcinomas, and carcinomas) of an organ (e.g., of lung, breast, lymphoid, gastrointestinal (e.g., colon), and genitourinary (e.g., renal, urothelial, or testicular tumors) tracts, pharynx, prostate, and ovary). In some embodiments, the cancer is a mesothelioma; neurofibromatosis; e.g., neurofibromatosis type 2, neurofibromatosis type 1; renal cancer; lung cancer, non small cell lung cancer; liver cancer; thyroid cancer; ovarian; breast cancer; a nervous system tumor; schwannoma; meningioma; schwannomatosis; neuroma acoustic; adenoid cystic carcinoma; ependymoma; or ependymal tumors. In some embodiments, the cancer is mesothelioma (e.g., malignant pleural mesothelioma, e.g., surgical resectable malignant pleural mesothelioma), breast cancer (e.g., triple negative breast cancer), ovarian cancer (e.g., advanced ovarian cancer), lung cancer (e.g., non-small cell lung cancer (NSCLC), e.g., KRAS mutant NSCLC)), or a non-hematolotic malignancy. In some embodiments, the cancer is melanoma (e.g., N-Ras mutated locally advanced or metastasis malignant cutaneous melanoma), colorectal cancer (e.g., metastatic colorectal cancer), leukemia (e.g., acute myeloid leukemia), adenocarcinoma (e.g., pancreatic adenocarcinoma), or a solid tumor (e.g., locally advanced solid tumor, metastatic solid tumor, hepatocellular carcinoma).

In some embodiments, the FAK inhibitor is administered orally.

In some embodiments, the FAK inhibitor is VS-4718, VS-5095, VS-6062, VS-6063, BI 853520, or GSK2256098.

In some embodiments, the FAK inhibitor is VS-4718. In some embodiments, the FAK inhibitor is VS-6063.

In some embodiments, the FAK inhibitor is administered at least once a day. In some embodiments, the FAK inhibitor is administered once a day. In some embodiments, the FAK inhibitor is administered twice a day.

In some embodiments, the FAK inhibitor is administered at about 100 mg to about 2000 mg.

In some embodiments, the FAK inhibitor is VS-6063 and the FAK inhibitor is administered at about 200 mg to about 600 mg twice a day. In some embodiments, VS-6063 is administered before or after (e.g., immediately before or immediately after) consumption of food.

In some embodiments, the FAK inhibitor is VS-4718 and the FAK inhibitor is administered at about 300 mg to about 500 mg once a day. In some embodiments, the FAK inhibitor is VS-4718 and the FAK inhibitor is administered at about 200 mg to about 400 mg twice a day.

In some embodiments, the immunotherapeutic agent is administered parenterally.

In some embodiments, the immunotherapeutic agent is an anti-CTLA-4 antibody (e.g., ipilimumab, tremelimumab). In some embodiments, the immunotherapeutic agent is an anti-PD-1 ligand (e.g., PD-LI (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1, e.g., nivolumab (i.e., MDX-1106, BMS-936558, ONO-4538); CT-011; AMP-224; pembrolizumab; pidilizumab; or MK-3475). In some embodiments, the immunotherapeutic agent is an anti-PD-L1 antibody (e.g., BMS936559 (i.e., MDX-1105); MEDI4736; MSB0010718C (avelumab); or MPDL-3280A). In some embodiments, the immunotherapeutic agent is a checkpoint blocking antibody (e.g., IMP321, MGA271). In some embodiments, the immunotherapeutic agent is an anti-CTLA-4 antibody (e.g., ipilimumab, tremelimumab, anti-TIM3, anti-LAG3, anti-TIGIT). In some embodiments, the immunotherapeutic agent is a cell-based therapy. In some embodiments, the cell-based therapy is a CAR-T therapy. In some embodiments, the immunotherapeutic agent is a co-stimulatory antibody (e.g., anti-4-1BB, anti-OX40, anti-GITR, anti-CD27, anti-CD40). In some embodiments, the method further comprises administering an additional chemotherapeutic agent or radiation therapy. In some embodiments, the method further comprises administering a cytotoxic agent. In some embodiments, the cytotoxic agent is gemcitabine or paclitaxel (e.g., nab-paclitaxel). In some embodiments, the immunotherapeutic agent is a co-stimulatory antibody (e.g., anti-4-1BB, anti-OX40, anti-GITR, anti-CD27, anti-CD40).

In some embodiments, the method further comprises administering an additional chemotherapeutic agent or radiation therapy. In some embodiments, the additional therapeutic agent is selected from: Alkylating agents, Antimetabolites, Antibiotics, Hormonal therapy agents, Plant derived anti-tumor substances, Cytotoxic topoisomerase inhibiting agents, Immunologicals, Biological response modifiers, Other anticancer agents, Other anti-angiogenic compounds, Platinum-coordinated compounds, Tyrosine kinase inhibitors, Antibodies, and Interferons.

In some embodiments, the FAK inhibitor is administered before the immunotherapeutic agent is administered. In some embodiments, the FAK inhibitor is administered after the immunotherapeutic agent is administered. In some embodiments, the FAK inhibitor is administered concurrently with the immunotherapeutic agent is administered.

In some embodiments, the subject has been previously treated with a chemotherapeutic agent or with radiation therapy. In some embodiments, the subject has failed (e.g., relapsed from, insensitive to, received no or little benefit from) conventional or standard cancer treatment (e.g., surgery, first-line therapy for cancer). In some embodiments, the subject has failed (e.g., relapsed from, insensitive to, received no or little benefit from) first-line treatment (e.g., first-line therapy for cancer).

In some embodiments, the subject is identified to have high PD-L1 or PD-L2, e.g., high PD-L1 or PD-L2 in tumor cells. In some embodiments, the subject is identified to have low PD-L1 or PD-L2, e.g., low PD-L1 or PD-L2 in tumor cells. In some embodiments, the subject is identified to express interferon gamma-induced (IFN-γ) genes.

DETAILED DESCRIPTION OF THE INVENTION

Described herein are methods for treating abnormal cell growth, e.g., cancer, e.g., a cancer described herein, the method comprising administering a FAK inhibitor and a cancer immunotherapy. Applicants have discovered that treatment of a subject suffering from abnormal cell growth, e.g., cancer, with a FAK inhibitor in combination with a cancer immunotherapy, more effectively prevents and treats abnormal cell growth, e.g., cancer, than with either agent alone.

Methods of Treatment and Administration

The methods described herein relate to treating a human subject suffering from a disease or disorder described herein (e.g., abnormal cell growth, e.g., cancer (e.g., a cancer described herein)) with a FAK inhibitor in combination with a cancer immunotherapy. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the method comprises administration of a FAK inhibitor before administration of a cancer immunotherapy. In some embodiments, the method comprises administration of a FAK inhibitor after administration of a cancer immunotherapy. In some embodiments, the method comprises administration of a FAK inhibitor concurrently with administration of a cancer immunotherapy. In some embodiments, the FAK inhibitor is VS-4718 (PND-1186), VS-6063 (PF-04554878; defactinib), VS-6062 (PF-562271), VS-5095, GSK2256098 or BI 853520.

Abnormal Cell Growth

The methods described herein are directed to the treatment or prevention of abnormal cell growth in a subject (e.g., a human subject). Abnormal cell growth, as used herein and unless otherwise indicated, refers to cell growth that is independent of normal regulatory mechanisms (e.g., loss of contact inhibition). This includes the abnormal growth of: (1) tumor cells (tumors) that proliferate, for example, by expressing a mutated tyrosine kinase or overexpression of a receptor tyrosine kinase; (2) benign and malignant cells of other proliferative diseases, for example, in which aberrant tyrosine kinase activation occurs; (3) any tumors that proliferate, for example, by receptor tyrosine kinases; (4) any tumors that proliferate, for example, by aberrant serine/threonine kinase activation; and (5) benign and malignant cells of other proliferative diseases, for example, in which aberrant serine/threonine kinase activation occurs. Abnormal cell growth can refer to cell growth in epithelial (e.g., carcinomas, adenocarcinomas); mesenchymal (e.g., sarcomas (e.g. leiomyosarcoma, Ewing's sarcoma)); hematopoetic (e.g., lymphomas, leukemias, myelodysplasias (e.g., pre-malignant)); or other (e.g., melanoma, mesothelioma, and other tumors of unknown origin) cells.

In some embodiments, the method is effective in treating non-hematolotic malignancies. In some embodiments, the method is effective in treating pancreas, non small cell lung carcinoma (NSCLC), small cell lung carcinoma (SCLC), mesothelioma, melanoma, breast and ovarian cancer. In an embodiment, the breast cancer is triple-negative breast cancer (e.g., breast cancer which does not express the genes for the estrogen receptor, progesterone receptor, and Her2/neu). In an embodiment, the lung cancer is non-small cell lung cancer (NSCLC), e.g., KRAS mutant NSCLC. In an embodiment, the ovarian cancer is advanced ovarian cancer (e.g., advanced ovarian cancer or metastatic ovarian cancer). In an embodiment, the method is effective in treating mesothelioma (e.g., malignant pleural mesothelioma, e.g., surgically resectable malignant pleural mesothelioma).

Neoplastic Disorders

Abnormal cell growth can refer to a neoplastic disorder. A "neoplastic disorder" is a disease or disorder characterized by cells that have the capacity for autonomous growth or replication, e.g., an abnormal state or condition characterized by proliferative cell growth. An abnormal mass of tissue as a result of abnormal cell growth or division, or a "neoplasm," can be benign, pre-malignant (carcinoma in situ) or malignant (cancer).

Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Treatment with the compound may be in an amount effective to ameliorate at least one symptom of the neoplastic disorder, e.g., reduced cell proliferation, reduced tumor mass, etc.

Cancer

The inventive methods of the present invention may be useful in the prevention and treatment of cancer, including for example, solid tumors, soft tissue tumors, and metastases thereof. The disclosed methods are also useful in treating non-solid cancers. Exemplary solid tumors include but are not limited to, malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include but are not limited to, colorectal cancers, renal-cell carcinoma, liver cancer (e.g., Hepatocellular carcinoma), non-small cell carcinoma of the lung, pancreatic (e.g., metastatic pancreatic adenocarcinoma) and cancer of the small intestine.

The cancer can include mesothelioma; neurofibromatosis; e.g., neurofibromatosis type 2, neurofibromatosis type 1; renal cancer; lung cancer, non small cell lung cancer; liver cancer; thyroid cancer; ovarian; breast cancer; a nervous system tumor; schwannoma; meningioma; schwannomatosis; neuroma acoustic; adenoid cystic carcinoma; ependymoma; or ependymal tumors. In some embodiments, the cancer exhibits decreased merlin expression and/or mutation, and/or deletion and/or promotor hypermethylation of the NF-2 gene. In an embodiment, the cancer is mesothelioma that exhibits decreased merlin expression and/or mutation, and/or deletion and/or promotor hypermethylation of the NF-2 gene.

In some embodiments, the cancer is renal cancer.

The cancer can include cancers characterized as comprising cancer stem cells, cancer associated mesenchymal cells, or tumor initiating cancer cells. The cancer can include cancers that have been characterized as being enriched with cancer stem cells, cancer associated mesenchymal cells, or tumor initiating cancer cells (e.g., a tumor enriched with cells that have undergone an epithelial-to-mesenchymal transition or a metastatic tumor).

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

The cancer can also include for example, but is not limited to, epithelial cancers, breast, lung, pancreatic, colorectal (e.g., metastatic colorectal, e.g., metastatic K Ras mutated), prostate, head and neck, melanoma (e.g., N Ras mutated locally advanced or metastatic malignant cutaneous melanoma), acute myelogenous leukemia, and glioblastoma. Exemplary breast cancers include but are not limited to, triple negative breast cancer, basal-like breast cancer, claudin-low breast cancer, invasive, inflammatory, metaplastic, and advanced Her-2 positive or ER-positive cancers resistant to therapy.

Other cancers include but are not limited to, brain, abdominal, esophagus, gastrointestinal, glioma, liver, tongue, neuroblastoma, osteosarcoma, ovarian, retinoblastoma, Wilm's tumor, multiple myeloma, skin, lymphoma, blood and bone marrow cancers (e.g., advanced hematological malignancies, leukemia, e.g., acute myeloid leukemia (e.g., primary or secondary), acute lymphoblastic leukemia, acute lymphocytic leukemia, T cell leukemia, hematological malignancies, advanced myeloproliferative disorders, myelodysplastic syndrome, relapsed or refractory multiple myeloma, advanced myeloproliferative disorders), retinal, bladder, cervical, kidney, endometrial, meningioma, lymphoma, skin, uterine, lung, non small cell lung, nasopharyngeal carcinoma, neuroblastoma, solid tumor, hematologic malignancy, squamous cell carcinoma, testicular, thyroid, mesothelioma, brain vulval, sarcoma, intestine, oral, endocrine, salivary, spermatocytic seminoma, sporadic medulalry thyroid carcinoma, non-proliferating testes cells, cancers related to malignant mast cells, non-Hodgkin's lymphoma, and diffuse large B cell lymphoma.

Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primaiy; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood;

Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated and/or prevented in accordance with the methods described herein.

In some embodiments, the tumor is a tumor of the hematopoietic and lymphoid tissues or a tumor that affects the blood, bone marrow, lymph, and lymphatic system. Hematological malignancies include acute lymphoblastic leukemia, acute myelogenous leukemia, chronic lymphocytic leukemia, chronic myelogenous leukemia, acute monocytic leukemia, other leukemias, Hodgkin's lymphomas, and Non-Hodgkin's lymphomas.

In some embodiments, the tumor is a solid tumor. In some embodiments, the solid tumor is locally advanced or metastatic. In some embodiments, the solid tumor is refractory (e.g., resistant) after standard therapy.

Methods described herein can reduce, ameliorate or altogether eliminate the disorder, and/or its associated symptoms, to keep it from becoming worse, to slow the rate of progression, or to minimize the rate of recurrence of the disorder once it has been initially eliminated (i.e., to avoid a relapse). A suitable dose and therapeutic regimen may vary depending upon the specific compounds, combinations, and/or pharmaceutical compositions used and the mode of delivery of the compounds, combinations, and/or pharmaceutical compositions. In some embodiments, the method increases the average length of survival, increases the average length of progression-free survival, and/or reduces the rate of recurrence, of subjects treated with the combinations described herein in a statistically significant manner.

In some embodiments, the cancer is lung cancer (e.g., non-small cell lung cancer (NSCLC), e.g., KRAS mutant NSCLC; metastatic cancer), bone cancer, pancreatic cancer, skin cancer, cancer of the head or neck, cutaneous or intraocular melanoma, uterine cancer, ovarian cancer (e.g., unresectable low-grade ovarian, advanced or metastatic ovarian cancer), rectal cancer, cancer of the anal region, stomach cancer, colon cancer, breast cancer (e.g., triple-negative breast cancer (e.g., breast cancer which does not express the genes for the estrogen receptor, progesterone receiptor, and Her2/neu)), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney (e.g., Wilms tumor, rhabdoid tumor; nephroma (e.g., mesoblastic nephroma)) or ureter, renal cell carcinoma, carcinoma of the renal pelvis, neoplasms of the central nervous system (CNS), primary CNS lymphoma, spinal axis tumors, brain stem glioma, pituitary adenoma, mesothelioma (e.g., malignant pleural mesothelioma, e.g., surgical resectable malignant pleural mesothelioma) or a combination of one or more of the foregoing cancers. In some embodiments, the cancer is ovarian cancer, pancreatic cancer, non-small cell lung cancer, head and neck cancer. In some embodiments, the cancer is metastatic. In some embodiments, the abnormal cell growth is locally recurring (e.g., the subject has a locally recurrent disease, e.g., cancer).

Inventive methods of the present invention contemplate single as well as multiple administrations of a therapeutically effective amount of a FAK inhibitor in combination with an immunotherapy. Combinations, e.g., a combination as described herein, e.g., a FAK inhibitor in combination with an immunotherapy, can be administered at regular intervals, depending on the nature, severity and extent of the subject's condition. In some embodiments, a combination as described herein, e.g., a FAK inhibitor in combination with an immunotherapy, is administered in a single dose. In some embodiments, a combination as described herein, e.g., a FAK inhibitor in combination with an immunotherapy, is administered in multiple doses. In some embodiments, a therapeutically effective amount of a combination as described herein, e.g., a FAK inhibitor in combination with an immunotherapy, may be administered orally and periodically at regular intervals (e.g., 1, 2, 3, 4, 5, 6, 7, 8, 9, 10 or more times every 1, 2, 3, 4, 5, or 6 days, or every 1, 2, 3, 4, 5, 6, 7, 8, or 9 weeks, or every 1, 2, 3, 4, 5, 6, 7, 8, 9 months or longer).

In some embodiments, a combination as described herein, e.g., a FAK inhibitor in combination with an immunotherapy, is administered at a predetermined interval (e.g., 1, 2, 3, 4, 5, 6, 7, 8, 9, 10 or more times every 1, 2, 3, 4, 5, or 6 days, or every 1, 2, 3, 4, 5, 6, 7, 8, or 9 weeks, or every 1, 2, 3, 4, 5, 6, 7, 8, 9 months or longer).

Compounds

The methods described herein comprise administering a FAK inhibitor and an immunotherapy to a subject having abnormal cell growth. Exemplary compounds that inhibit FAK include, but are not limited to the following:

FAK Inhibitors

Potent inhibitors of the FAK protein tyrosine kinases may be adapted to therapeutic use as antiproliferative agents (e.g., anticancer), antitumor (e.g., effective against solid tumors), antiangiogenesis (e.g., stop or prevent proliferation of blood vessels) in mammals, particularly in humans. The compounds described herein, e.g., FAK inhibitors, may be useful in the prevention and treatment of a disease or disorder described herein (e.g., abnormal cell growth, e.g., cancer (e.g., a cancer described herein)). The compounds described herein, e.g., FAK inhibitors, may be useful in the prevention and treatment of non-hematolotic malignancies, a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH), and in the prevention and treatment of disorders such as mesothelioma. In some embodiments, the compounds described herein, e.g., FAK inhibitors, inhibit protein tyrosine kinase 2 (PYK2).

In some embodiments, the compounds described herein, or pharmaceutically acceptable salts thereof, are present in a composition in the amount of 5, 10, 11, 12, 12.5, 13, 14, 15, 20, 25, 30, 35, 40, 45, 50, 55, 60% w/w or greater. In some embodiments, the compounds described herein, or pharmaceutically acceptable salts thereof, is present in a composition in the amount from about 5% to 60%, 5% to 50%, 10% to 50%, 10% to 40% w/w.

The following examples of FAK inhibitors include, but shall not be construed to be limited to:

Compounds VS-4718 and VS-5095

Exemplary FAK inhibitors include but are not limited to VS-4718, VS-5095, and related compounds, or a pharmaceutically acceptable salt thereof. Compounds VS-4718, VS-5095, and related compounds are described in PCT/US2010/045359 and US20110046121, the contents of each of which are incorporated herein in their entirety. A compound of Formula (I-a) is also referred to as VS-4718. A compound of Formula (I-b) is also referred to as VS-5095. In some embodiments, the FAK inhibitor is a compound of Formula (I-a) or (I-b):

Formula (I-a)

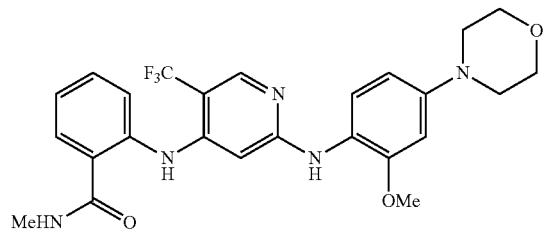

Formula (I-b)

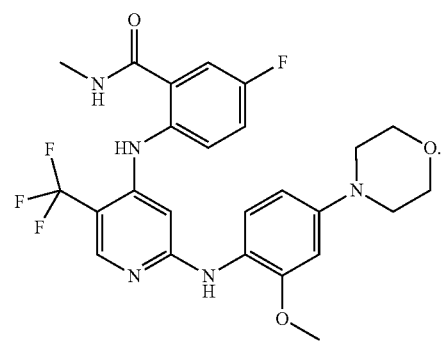

Exemplary FAK inhibitors also include but are not limited to GSK2256098 and related compounds, or a pharmaceutically acceptable salt thereof. GSK2256098 and related compounds are described in US20100113475, US20100317663, US20110269774, US20110207743, US20140155410, and US20140107131, the contents of which are incorporated herein in their entirety. In some embodiments, the FAK inhibitor is a compound of Formula (I-c1), (I-c2), (I-c3), (I-c4), or (I-c5):

Formula (I-c1)

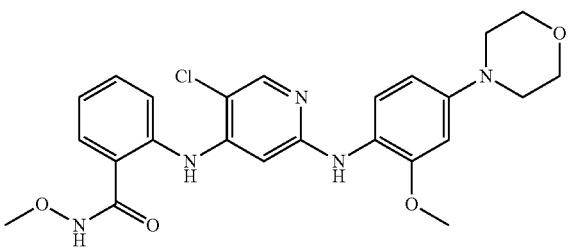

Formula (I-c2)

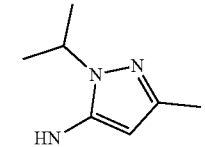

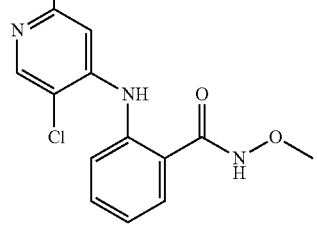

Formula (I-c3)

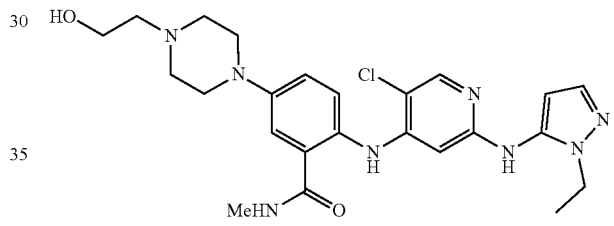

Formula (I-c4)

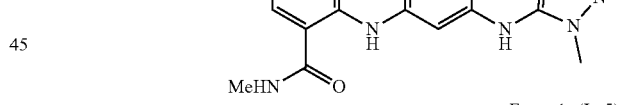

Formula (I-c5)

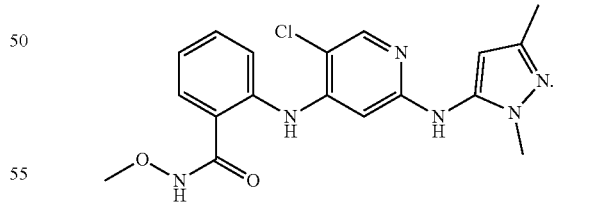

Compound VS-6063 and VS-6062

Exemplary FAK inhibitors also include but are not limited to VS-6063, VS-6062, and related compounds, or a pharmaceutically acceptable salt thereof (e.g., VS-6063 hydrochloride, VS-6062 hydrochloride). VS-6063, VS-6062, and related compounds are also disclosed in, e.g., U.S. Pat. No. 7,928,109, EP1578732, PCT/IB2004/202744, PCT/IB2003/005883, PCT/IB2005/001201, and PCT/IB2006/003349, the contents of each of which are incorporated herein by reference. VS-6063 is also known as a compound of Formula (I-d), defactinib and PF-04554878. VS-6062 is also known as a compound of Formula (I-d) and PF-00562271. In some embodiments, the FAK inhibitor is a compound of Formula (I-d) or (I-e):

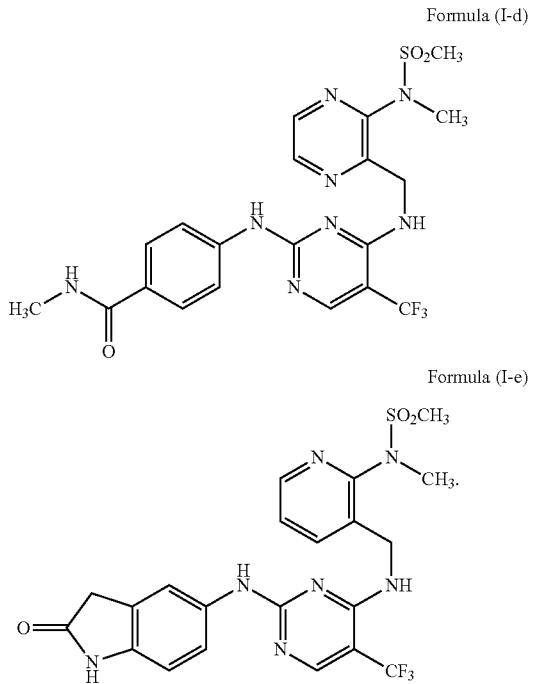

Other FAK Inhibitors

Exemplary FAK inhibitors also include but are not limited to a compound of Formula (I-f), Formula (I-g), and related compounds, or a pharmaceutically acceptable salt thereof. A compound of Formula (I-f) and related compounds are described in U.S. Pat. No. 8,569,298, the contents of which are incorporated herein in their entirety. In some embodiments, the FAK inhibitor is 2-[[2[(1,3-dimethylpyrazol-4-yl)amino]-5-(trifluoromethyl)-4-pyridyl]amino]-5-fluoro-N-methoxy-benzamide, or a compound of Formula (I-f):

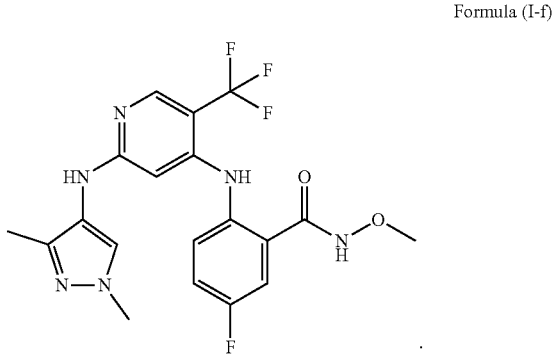

In some embodiments, the FAK inhibitor is BI 853520.

Immunotherapy

The methods described herein comprise administering a FAK inhibitor and an immunotherapy to a subject having abnormal cell growth. Exemplary immunotherapies include, but are not limited to the following.

In some embodiments, the immunotherapeutic agent is a compound (e.g., a ligand, an antibody) that inhibits the immune checkpoint blockade pathway. Cancer immunotherapy refers to the use of the immune system to treat cancer. Three main groups of immunotherapy used to treat cancer includes cell-based, antibody-based, and cytokine therapies. All groups exploit cancer cells' display of subtly different structures (e.g., molecular structure; antigens, proteins, molecules, carbohydrates) on their surface that can be detected by the immune system. Cancer immunotherapy (i.e., anti-tumor immunotherapy or anti-tumor immunotherapeutics) include but are not limited to, immune checkpoint antibodies (e.g., PD-1 antibodies, PD-L1 antibodies, PD-L2 antibodies, CTLA-4 antibodies, TIM3 antibodies, LAG3 antibodies, TIGIT antibodies); and cancer vaccines (i.e., anti-tumor vaccines).

Cell-based therapies (e.g., cancer vaccines), usually involve the removal of immune cells from a subject suffering from cancer, either from the blood or from a tumor. Immune cells specific for the tumor will be activated, grown, and returned to a subject suffering from cancer where the immune cells provide an immune response against the cancer. Cell types that can be used in this way are e.g., natural killer cells, lymphokine-activated killer cells, cytotoxic T-cells, dendritic cells, CAR-T therapies (i.e., chimeric antigen receptor T-cells which are T-cells engineered to target specific antigens), TIL therapy (i.e., administration of tumor-infiltrating lymphocytes), TCR gene therapy, protein vaccines, and nucleic acid vaccines. An exemplary cell-based therapy is Provenge. In some embodiments, the cell-based therapy is a CAR-T therapy.

Interleukin-2 and interferon-alpha are examples of cytokines, proteins that regulate and coordinate the behavior of the immune system.

Antibody therapies are antibody proteins produced by the immune system and that bind to a target antigen on the surface of a cell. Antibodies are typically encoded by an immunoglobulin gene or genes, or fragments thereof. In normal physiology antibodies are used by the immune system to fight pathogens. Each antibody is specific to one or a few proteins, and those that bind to cancer antigens are used, e.g., for the treatment of cancer. Antibodies are capable of specifically binding an antigen or epitope. (Fundamental Immunology, 3$^{rd}$ Edition, W. e., Paul, ed., Raven Press, N.Y. (1993). Specific binding occurs to the corresponding antigen or epitope even in the presence of a heterogeneous population of proteins and other biologics. Specific binding of an antibody indicates that it binds to its target antigen or epitope with an affinity that is substantially greater than binding to irrelevant antigens. The relative difference in affinity is often at least 25% greater, more often at least 50% greater, most often at least 100% greater. The relative difference can be at least 2-fold, at least 5-fold, at least 10-fold, at least 25-fold, at least 50-fold, at least 100-fold, or at least 1000-fold, for example.

Exemplary types of antibodies include without limitation human, humanized, chimeric, monoclonal, polyclonal, single chain, antibody binding fragments, and diabodies. Once bound to a cancer antigen, antibodies can induce antibody-dependent cell-mediated cytotoxicity, activate the complement system, prevent a receptor interacting with its ligand or deliver a payload of chemotherapy or radiation, all of which can lead to cell death. Exemplary antibodies for the treatment of cancer include but are not limited to, Alemtuzumab, Bevacizumab, Bretuximab vedotin, Cetuximab, Gemtuzumab ozogamicin, Ibritumomab tiuxetan, Ipilimumab, Ofatumumab, Panitumumab, Rituximab, Tositumomab, Trastuzumab, Nivolumab, Pembrolizumab, Avelumab, durvalumab and pidilizumab.

Checkpoint Blocking Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a compound (e.g., an inhibitor or antibody) that inhibits the immune checkpoint blockade pathway. Immune checkpoint proteins, under normal physiological conditions, maintain self-tolerance (e.g., prevent autoimmunity) and protect tissues from damage when the immune system is responding to e.g., pathogenic infection. Immune checkpoint proteins can be dysregulated by tumors as an important immune resistance mechanism. (Pardoll, Nature Rev. Cancer, 2012, 12, 252-264). Agonists of co-stimulatory receptors or antagonists of inhibitory signals (e.g., immune checkpoint proteins), provide an amplification of antigen-specific T-cell responses. Antibodies that block immune checkpoints do not target tumor cells directly but typically target lymphocyte receptors or their ligands to enhance endogenous antitumor activity.

Exemplary checkpoint blocking antibodies include but are not limited to, anti-CTLA-4, anti-PD-1, anti-LAG3 (i.e., antibodies against lymphocyte activation gene 3), and anti-TIM3 (i.e., antibodies against T-cell membrane protein 3). Exemplary anti-CTLA-4 antibodies include but are not limited to, ipilimumab and tremelimumab. Exemplary anti-PD-1 ligands include but are not limited to, PD-L1 (i.e., B7-H1 and CD274) and PD-L2 (i.e., B7-DC and CD273). Exemplary anti-PD-1 antibodies include but are not limited to, nivolumab (i.e., MDX-1106, BMS-936558, or ONO-4538)), CT-011, AMP-224, pembrolizumab (trade name Keytruda), and MK-3475. Exemplary PD-L1-specific antibodies include but are not limited to, BMS936559 (i.e., MDX-1105), MEDI4736 and MPDL-3280A. Exemplary checkpoint blocking antibodies also include but are not limited to, IMP321 and MGA271.

T-regulatory cells (e.g., CD4+, CD25+, or T-reg) are also involved in policing the distinction between self and non-self (e.g., foreign) antigens, and may represent an important mechanism in suppression of immune response in many cancers. T-reg cells can either emerge from the thymus (i.e., "natural T-reg") or can differentiate from mature T-cells under circumstances of peripheral tolerance induction (i.e., "induced T-reg"). Strategies that minimize the action of T-reg cells would therefore be expected to facilitate the immune response to tumors. (Sutmuller, van Duivernvoorde et al., 2001).

In some embodiments, the compounds (compounds described herein, e.g., a FAK inhibitor) and compositions (e.g., compositions comprising a compound described herein, e.g., a FAK inhibitor) are used with a cancer immunotherapy (e.g., a checkpoint blocking antibody) to treat a subject (e.g., a human subject), e.g., suffering from a disease or disorder described herein (e.g., abnormal cell growth, e.g., cancer (e.g., a cancer described herein)).

Inventive methods of the present invention contemplate single as well as multiple administrations of a therapeutically effective amount of a compound as described herein. Compounds, e.g., a compound as described herein, can be administered at regular intervals, depending on the nature, severity and extent of the subject's condition. In some embodiments, a compound described herein is administered in a single dose. In some embodiments, a compound described herein is administered in multiple doses.

Co-Stimulatory Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a co-stimulatory inhibitor or antibody. In some embodiments, the methods described herein comprise depleting or activating anti-4-1BB, anti-OX40, anti-GITR, anti-CD27 and anti-CD40, and variants thereof.

Additional Therapeutic Agents/Combination Therapy

The methods of the present invention may be administered in combination with an additional agent (e.g., therapeutic agent). The additional agent can include but are not limited to, an anti-tumor or anti-cancer agent, e.g., an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In some embodiments, the methods and compositions described herein (e.g., a FAK inhibitor in combination with an immunotherapy) is administered together with an additional therapy (e.g., cancer treatment). In one embodiment, a mixture of one or more compounds or pharmaceutical compositions may be administered with the combination described herein, e.g., a FAK inhibitor in combination with an immunotherapy, to a subject in need thereof. In yet another embodiment, one or more compounds or compositions (e.g., pharmaceutical compositions) may be administered with the combination described herein, e.g., a FAK inhibitor in combination with an immunotherapy, for the treatment or avoidance of various diseases, including, for example, cancer, diabetes, neurodegenerative diseases, cardiovascular disease, blood clotting, inflammation, flushing, obesity, aging, stress, etc. In various embodiments, combination therapies comprising a compound or pharmaceutical composition described herein may refer to (1) pharmaceutical compositions that comprise one or more compounds in combination with the combination described herein, e.g., a FAK inhibitor in combination with an immunotherapy; and (2) co-administration of one or more compounds or pharmaceutical compositions described herein with the combination described herein, e.g., a FAK inhibitor in combination with an immunotherapy, wherein the compound or pharmaceutical composition described herein have not been formulated in the same compositions. In some embodiments, the combinations described herein (e.g., a FAK inhibitor in combination with an immunotherapy) are administered with an additional treatment (e.g., an additional cancer treatment). In some embodiments, the additional treatment (e.g., an additional cancer treatment) can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional treatment (e.g., a compound or therapy). The order of administration of the first and secondary compound or therapy can also be reversed.

The methods of the invention may be used or administered in combination with one or more additional therapies (e.g., cancer treatment, e.g., surgery, additional drug(s) or therapeutic agents) for the treatment of the disorder/diseases mentioned. The additional therapies (e.g., cancer treatment, e.g., drug(s) or therapeutic agents described herein) can be administered in the same formulation or in separate formulations. If administered in separate formulations, the compounds of the invention may be administered sequentially or simultaneously with the other drug(s).

In addition to being able to be administered in combination with one or more additional therapies (e.g., cancer treatment, e.g., surgery, additional drug(s) or therapeutic agents), methods of the invention may be administered either simultaneously (as a combined preparation) or sequentially in order to achieve a desired effect. This is especially desirable where the therapeutic profile of each compound is different such that the combined effect of the two drugs provides an improved therapeutic result.

Exemplary cancer treatments include, for example: chemotherapy, targeted therapies such as antibody therapies, immunotherapy, and hormonal therapy. Examples of each of these treatments are provided below.

Chemotherapy

In some embodiments, the methods of the invention are administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

The methods of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of additional agents, e.g., additional therapeutic agents, that may be used with the methods of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals include but are not limited to, interferons and numerous other immune enhancing agents. Interferons include but are not limited to, interferon alpha, interferon alpha-2a, interferon, alpha-2b, interferon beta, interferon gamma-1a or interferon gamma-n1. Other agents include but are not limited to, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, and Provenge;

Biological response modifiers are agents that modify defense mechanisms of living organisms or biological responses, such as survival, growth, or differentiation of tissue cells to direct them to have anti-tumor activity. Such agents include but are not limited to, krestin, lentinan, sizofiran, picibanil, or ubenimex;

Other anticancer agents include but are not limited to, alitretinoin, ampligen, atrasentan, bexarotene, bortezomib, Bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, TLK-286, Velcade, Tarceva, or tretinoin;

Other anti-angiogenic compounds include but are not limited to, acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors include but are not limited to, Iressa or SU5416;

Antibodies include but are not limited to, Herceptin, Erbitux, Avastin, or Rituximab; and Interferons include but are not limited to, interferon alpha, interferon alpha-2a, interferon, alpha-2b, interferon beta, interferon gamma-1a or interferon gamma-n1.

Because some drugs work better together than alone, two or more drugs are often given at the same time or sequentially. Often, two or more chemotherapy agents are used as combination chemotherapy. In some embodiments, the chemotherapy agents (including combination chemotherapy) can be used in combination with the methods described herein.

Targeted Therapy

In some embodiments, the methods of the invention are administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-depdendent kinase inhibitors such as Alvocidib and Seliciclib. Monoclonal antibody therapy is another strategy in which the therapeutic agent is an antibody which specifically binds to a protein on the surface of the cancer cells. Examples include but are not limited to, the anti-HER2/neu antibody trastuzumab (HERCEPTIN®) typically used in breast cancer, and the anti-CD20 antibody rituximab and Tositumomab typically used in a variety of B-cell malignancies. Other exemplary anbitodies include but are not limited to, Ctuximab, Panitumumab, Trastuzumab, Alemtuzumab, Bevacizumab, Edrecolomab, and Gemtuzumab. Exemplary fusion proteins include but are not limited to, Aflibercept and Denileukin diftitox. Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®. In some embodiments, the targeted therapy can be used in combination with the methods of the invention.

Anti-Inflammatory Agents

The methods of the invention can be administered with an anti-inflammatory agent. Anti-inflammatory agents include, but are not limited to, non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates)(Mefenamic acid, Meclofenamic acid, Flufenamic acid, Tolfenamic acid), Selective COX-2 inhibitors (Coxibs) (Celecoxib), Sulphonanilides (Nimesulide). Steriods (e.g. Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate, Aldosterone).

Analgesic Agents

The methods of the invention can be administered with analgesic agents. Analgesics include but are not limited to, opiates (e.g. morphine, codeine, oxycodone, hydrocodone, dihydromorphine, pethidine, buprenorphine, tramadol, venlafaxine), paracetomal and non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates) (Mefenamic acid, Meclofenamic acid, Flufenamic acid, Tolfenamic acid), Selective COX-2 inhibitors (Coxibs) (Celecoxib), Sulphonanilides (Nimesulide).

Antiemetic Agents

The methods of the invention can be administered with an antiemetic agent. Antiemetic agents include, but are not limited to, 5-HT3 receptor antagonists (Dolasetron (Anzemet), Granisetron (Kytril, Sancuso), Ondansetron (Zofran), Tropisetron (Navoban), Palonosetron (Aloxi), Mirtazapine (Remeron)), Dopamine antagonists (Domperidone, Olanzapine, Droperidol, Haloperidol, Chlorpromazine, Promethazine, Prochlorperazine, Metoclopramide (Reglan), Alizapride, Prochlorperazine (Compazine, Stemzine, Buccastem, Stemetil, Phenotil), NK1 receptor antagonist (Aprepitant (Emend), Antihistamines (Cyclizine, Diphenhydramine (Benadryl), Dimenhydrinate (Gravol, Dramamine), Meclozine (Bonine, Antivert), Promethazine (Pentazine, Phenergan, Promacot), Hydroxyzine), benzodiazapines (Lorazepam, Midazolam), Anticholinergics (hyoscine), steriods (Dexamethasone).

Radiation Therapy

The methods of the invention are can be used in combination with directed energy or particle, or radioisotope treatments, e.g., radiation therapies, e.g., radiation oncology, for the treatment of proliferative disease, e.g., cancer, e.g., cancer associated with cancer stem cells. The methods of the invention may be administered to a subject simultaneously or sequentially along with the directed energy or particle, or radioisotope treatments. For example, the methods of the invention may be administered before, during, or after the directed energy or particle, or radioisotope treatment, or a combination thereof. The directed energy or particle therapy may comprise total body irradiation, local body irradiation, or point irradiation. The directed energy or particle may originate from an accelerator, synchrotron, nuclear reaction, vacuum tube, laser, or from a radioisotope. The therapy may comprise external beam radiation therapy, teletherapy, brachytherapy, sealed source radiation therapy, systemic radioisotope therapy, or unsealed source radiotherapy. The therapy may comprise ingestion of, or placement in proximity to, a radioisotope, e.g., radioactive iodine, cobalt, cesium, potassium, bromine, fluorine, carbon. External beam radiation may comprise exposure to directed alpha particles, electrons (e.g., beta particles), protons, neutrons, positrons, or photons (e.g., radiowave, millimeter wave, microwave, infrared, visible, ultraviolet, X-ray, or gamma-ray photons). The radiation may be directed at any portion of the subject in need of treatment.

Surgery

The methods of the invention can be used in combination with surgery, e.g., surgical exploration, intervention, biopsy, for the treatment of proliferative disease, e.g., cancer, e.g., cancer associated with cancer stem cells. The methods of the invention may be administered to a subject simultaneously or sequentially along with the surgery. For example, the methods of the invention may be administered before (pre-operative), during, or after (post-operative) the surgery, or a combination thereof. The surgery may be a biopsy during which one or more cells are collected for further analysis. The biopsy may be accomplished, for example, with a scalpel, a needle, a catheter, an endoscope, a spatula, or scissors. The biopsy may be an excisional biopsy, an incisional biopsy, a core biopsy, or a needle biopsy, e.g., a needle aspiration biopsy. The surgery may involve the removal of localized tissues suspected to be or identified as being cancerous. For example, the procedure may involve the removal of a cancerous lesion, lump, polyp, or mole. The procedure may involve the removal of larger amounts of tissue, such as breast, bone, skin, fat, or muscle. The procedure may involve removal of part of, or the entirety of, an organ or node, for example, lung, throat, tongue, bladder, cervix, ovary, testicle, lymph node, liver, pancreas, brain, eye, kidney, gallbladder, stomach, colon, rectum, or intestine. In one embodiment, the cancer is breast cancer, e.g., triple negative breast cancer, and the surgery is a mastectomy or lumpectomy.

First-Line Therapy

The present invention describes a method of treating a human subject having cancer, wherein the subject has failed (e.g., relapsed from, insensitive to, received no or little benefit from) first-line treatment (e.g., first-line therapy for cancer). The present invention also describes a method of treating a human subject having cancer, wherein the methods of the invention are administered with an additional agent. In some embodiments, the additional agent is a first-line therapy for cancer.

First-line therapy is typically the first treatment given for a disease (e.g., cancer as described herein). It is often part of a standard set of treatments, such as surgery followed by chemotherapy and radiation. When used by itself, first-line therapy is generally the one accepted as the best treatment. If it does not cure the disease or it causes severe side effects, other treatment(s) may be added or used instead. First-line therapy is also called induction therapy, primary therapy, and primary treatment.

For example, first-line-therapy, e.g., for Hodgkin lymphoma may include: Adcetris (Brentuximab Vedotin), Adriamycin PFS (Doxorubicin Hydrochloride), Adriamycin RDF (Doxorubicin Hydrochloride), Ambochlorin (Chlorambucil), Amboclorin (Chlorambucil), Blenoxane (Bleomycin), Bleomycin, Brentuximab Vedotin, Chlorambucil, Clafen (Cyclophosphamide), Cyclophosphamide, Cytoxan (Cyclophosphamide), Dacarbazine, Doxorubicin Hydrochloride, DTIC-Dome (Dacarbazine), Leukeran (Chlorambucil), Linfolizin (Chlorambucil), Lomustine, Matulane (Procarbazine Hydrochloride), Neosar (Cyclophosphamide), Procarbazine Hydrochloride, Velban (Vinblastine Sulfate), Velsar (Vinblastine Sulfate), Vinblastine Sulfate, Vincasar PFS (Vincristine Sulfate), and Vincristine Sulfate.

In some embodiments, first-line-therapy, e.g., for Hodgkin lymphoma comprises administration of a combination of therapeutic agents, e.g., therapeutic agents as described herein. For example, the combination may comprise Doxorubicin Hydrochloride (Adriamycin), Bleomycin, Vinblastine Sulfate, and Dacarbazine (i.e., ABVD). As another example, the combination may comprise Doxorubicin Hydrochloride (Adriamycin), Bleomycin, Vinblastine Sulfate, and Etoposide (i.e., ABVE). In some embodiments, the combination comprises Doxorubicin Hydrochloride (Adriamycin), Bleomycin, Vinblastine Sulfate, Etoposide, Prednisone, and Cyclophosphamide (i.e., ABVE-PC). In some embodiments, the combination comprises Vincristine Sulfate, Doxorubicin Hydrochloride (Adriamycin), Methotrexate, and Prednisone (i.e., VAMP).

Approved therapeutic agents and combinations for different types of cancer can be found on the National Cancer Institute at the National Institutes of Health Cancer website at http://www.cancer.gov/cancertopics/druginfo/drug-page-index Second-Line Therapy The present invention describes a method of treating a human subject having cancer, wherein the subject has failed (e.g., relapsed from, insensitive to, received no or little benefit from) second-line treatment (e.g., second-line therapy for cancer). The present invention also describes a method of treating a human subject having cancer, wherein the methods of the invention are administered with an additional agent. In some embodiments, the additional agent is a first or second line therapy for cancer. Second-line therapy generally refers to treatment that is given when initial treatment (e.g., first-line therapy) does not achieve a desired result, e.g., does not work, is not efficacious; stops working. Second-line therapy is typically considered or given when a subject does not respond or develops a resistance to initial treatment (e.g., first-line therapy). For example, second-line therapy is typically considered or given to a subject with relapsed or refractory disease.

Administration and Dosage

The methods of this invention comprise administration of compounds described herein (e.g., a composition comprising a compound described herein). The compounds described herein may be administered orally, parenterally, topically, rectally, or via an implanted reservoir, preferably by oral administration or administration by injection. In some cases, the compound is administered as a composition comprising a compound described herein. In some embodiments, the pH of the composition (e.g., pharmaceutical composition) may be adjusted with pharmaceutically acceptable acids, bases or buffers to enhance the stability or efficacy of the composition.

In some embodiments, the subject is administered a composition comprising a compound as described herein, e.g., a FAK inhibitor (e.g., a FAK inhibitor as described herein) orally.

In some embodiments, the subject is administered a composition comprising an immunotherapy (an immunotherapy as described herein), parenterally (e.g., intravenously).

Oral Administration

The methods described herein comprise administering to a subject a composition (e.g., pharmaceutical composition) comprising a FAK inhibitor and a composition comprising an immunotherapeutic agent. In some embodiments, the subject is administered the composition comprising a FAK inhibitor orally. In some embodiments the composition (e.g., pharmaceutical composition) is be orally administered in any orally acceptable dosage form including, but not limited to, liqui-gel tablets or capsules, syrups, emulsions and aqueous suspensions. Liqui-gels may include gelatins, plasticisers, and/or opacifiers, as needed to achieve a suitable consistency and may be coated with enteric coatings that are approved for use, e.g., shellacs. Additional thickening agents, for example gums, e.g., xanthum gum, starches, e.g., corn starch, or glutens may be added to achieve a desired consistency of the composition (e.g., pharmaceutical composition) when used as an oral dosage. If desired, certain sweetening and/or flavoring and/or coloring agents may be added. In some embodiments, the subject is administered the composition comprising a FAK inhibitor orally.

In some embodiments, the subject is administered the composition (e.g., pharmaceutical composition) in a form suitable for oral administration such as a tablet, capsule, pill, powder, sustained release formulations, solution, and suspension. The composition (e.g., pharmaceutical composition) may be in unit dosage forms suitable for single administration of precise dosages. Pharmaceutical compositions may comprise, in addition to a compound as described herein (e.g., a FAK inhibitor (e.g., VS-6063 or a pharmaceutically acceptable salt thereof); a pharmaceutically acceptable carrier, and may optionally further comprise one or more pharmaceutically acceptable excipients, such as, for example, stabilizers, diluents, binders, and lubricants. In addition, the tablet may include other medicinal or pharmaceutical agents, carriers, and or adjuvants. Exemplary pharmaceutical compositions include compressed tablets (e.g., directly compressed tablets), e.g., comprising a FAK inhibitor (e.g., VS-6063 or a pharmaceutically acceptable salt thereof).

Tablets are also provided comprising the active or therapeutic ingredient (e.g., compound as described herein (e.g., a FAK inhibitor (e.g., VS-6063 or a pharmaceutically acceptable salt thereof). In addition to the active or therapeutic ingredients, tablets may contain a number of inert materials such as carriers. Pharmaceutically acceptable carriers can be sterile liquids, such as water and oils, including those of petroleum, animal, vegetable or synthetic origin, such as peanut oil, sesame oil and the like. Saline solutions and aqueous dextrose can also be employed as liquid carriers. Oral dosage forms for use in accordance with the present invention thus may be formulated in conventional manner using one or more pharmaceutically acceptable carriers comprising excipients and auxiliaries, which facilitate processing of the active ingredients into preparations which, can be used pharmaceutically.

Excipients can impart good powder flow and compression characteristics to the material being compressed. Examples of excipients are described, for example, in the Handbook of Pharmaceutical Excipients (5$^{th}$ edition), Edited by Raymond C Rowe, Paul J. Sheskey, and Sian C. Owen; Publisher: Pharmaceutical Press.

For oral administration, the active ingredients, e.g., the compound as described herein (e.g., a FAK inhibitor (e.g., VS-6063 or a pharmaceutically acceptable salt thereof); can be formulated readily by combining the active ingredients with pharmaceutically acceptable carriers well known in the art. Such carriers enable the active ingredients of the invention to be formulated as tablets, pills, capsules, liquids, gels, syrups, slurries, powders or granules, suspensions or solutions in water or non-aqueous media, and the like, for oral ingestion by a subject. Pharmacological preparations for oral use can be made using a solid excipient, optionally grinding the resulting mixture, and processing the mixture of granules, after adding suitable auxiliaries if desired, to obtain, for example, tablets. Suitable excipients such as diluents, binders or disintegrants may be desirable.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics"). Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician. A course of therapy can comprise one or more separate administrations of a compound as described herein (e.g., a FAK inhibitor, an immunotherapy). A course of therapy can comprise one or more cycles of a compound as described herein (e.g., a FAK inhibitor, an immunotherapy).

In some embodiments, a cycle, as used herein in the context of a cycle of administration of a drug, refers to a period of time for which a drug is administered to a patient. For example, if a drug is administered for a cycle of 21 days, the periodic administration, e.g., daily or twice daily, is given for 21 days. A drug can be administered for more than one cycle. Rest periods may be interposed between cycles. A rest cycle may be 1, 2, 4, 6, 8, 10, 12, 16, 20, 24 hours, 1, 2, 3, 4, 5, 6, 7 days, or 1, 2, 3, 4 or more weeks in length.

Oral dosage forms may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Parenteral Formulations

The methods described herein comprise administering to a subject a composition (e.g., pharmaceutical composition) comprising a FAK inhibitor and a composition comprising an immunotherapeutic agent. In some embodiments, the immunotherapeutic agent is administered parenterally (e.g., intravenously). In some embodiments, an immunotherapy described herein is formulated with a pharmaceutical excipient suitable for parenteral administration. Exemplary forms of parenteral administration include intravenous, intraarterial, subcutaneous, intramuscular, intravascular, intraperitoneal or infusion.

The forms in which an immunotherapy (e.g., an immunotherapy described herein) can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline can also be used for injection. Exemplary excipients include ethanol, glycerol, propylene glycol, liquid polyethylene glycol, cyclodextrin derivatives, and vegetable oils.

Sterile injectable solutions can be prepared by incorporating an immunotherapy (e.g., an immunotherapy described herein) in the required amount in the appropriate solvent with one or more excipients, followed by filtered sterilization. Dispersions can be prepared by incorporating a sterilized halofuginone or a pharmaceutically acceptable salt thereof into a sterile vehicle. An injectable formulation can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as described herein.

This disclosure is not limited in its application to the details of the compositions, e.g., combinations of compounds, or the specific order of preparation or administration of the compounds. The compounds, e.g., combinations of compounds, described herein may be suitably prepared using other techniques and/or administered in various ways. Also, the phraseology and terminology used herein is for the purpose of description and should not be regarded as limiting.

Definitions

As used herein, the articles "a" and "an" refer to one or to more than one (e.g., at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, an amount of a compound effective to treat a disease or disorder described herein (e.g., abnormal cell growth, e.g., cancer (e.g., a cancer described herein)), "effective amount" or "effective course" refers to an amount of the compound which is effective, upon single or multiple dose administration(s) to a subject, in treating a subject, or in curing, alleviating, relieving or improving a subject with a disease or disorder described herein (e.g., abnormal cell growth, e.g., cancer (e.g., a cancer described herein)) beyond that expected in the absence of such treatment (e.g., placebo treatment).

The term "pharmaceutically acceptable," as used herein, refers to a compound or carrier (e.g., excipient) that may be administered to a subject, together with a compound described herein, and which does not destroy the pharmacological activity thereof and is nontoxic when administered in doses sufficient to deliver a therapeutic amount of the compound.

The term, "pharmaceutically acceptable salts," as used herein, refers to derivatives of a compound described herein, wherein the compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the disclosure include but are not limited to, the conventional non-toxic salts of a compound described herein, formed, for example, from non-toxic inorganic or organic acids. The pharmaceutically acceptable salts of the disclosure can be synthesized from a compound described herein, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, $17^{th}$ ed., Mack Publishing Company, Easton, Pa., 1985, p. 1418 and *Journal of Pharmaceutical Science*, 66, 2 (1977), each of which is incorporated herein by reference in its entirety.

The term, "oral dosage form," as used herein, refers to a composition or medium used to administer an agent, e.g., a therapeutic agent, e.g., a compound as described herein, to a subject. Typically, an oral dosage form is administered via the mouth, however, "oral dosage form" is intended to cover any substance which is administered to a subject and is absorbed across a membrane, e.g., a mucosal membrane, of the gastrointestinal tract, including, e.g., the mouth, esophagus, stomach, small intestine, large intestine, and colon. For example, "oral dosage form" covers a solution which is administered through a feeding tube into the stomach.

The term, "treat" or "treatment," as used herein, refers to the application or administration of a compound, alone or in combination with, an additional agent to a subject, e.g., a subject who has a disease or disorder described herein (e.g., abnormal cell growth, e.g., cancer (e.g., a cancer described herein)) or is suffering from a disease or disorder described herein (e.g., abnormal cell growth, e.g., cancer (e.g., a cancer described herein)), a symptom of a disease or disorder described herein (e.g., abnormal cell growth, e.g., cancer (e.g., a cancer described herein)), or a predisposition toward a disease or disorder described herein (e.g., abnormal cell growth, e.g., cancer (e.g., a cancer described herein)), with the purpose to cure, heal, alleviate, relieve, alter, remedy, ameliorate, improve or affect the disease or disorder described herein (e.g., abnormal cell growth, e.g., cancer (e.g., a cancer described herein)).

As used herein, "administered in combination", "co-administration", "co-administering" means that two or more agents are administered to a subject at the same time or within an interval, such that there is overlap of an effect of each agent on the subject. Preferably the administrations of the agents are spaced sufficiently close together such that a combinatorial effect is achieved. The interval can be an interval of minutes, hours, days or weeks. Generally, the agents are concurrently bioavailable, e.g., detectable, in the subject. The first, second, and third agents can be administered in any order, or as one or more preparations that includes two more of the agents. In a preferred embodiment, at least one administration of one of the agents, e.g., the first agent, is made within minutes, one, two, three, or four hours, or even within one or two days of the other agent, e.g., the second agent or third agent. In some cases, combinations can achieve synergistic results, i.e., greater than additive results, e.g., at least 20, 50, 70, or 100% greater than additive.

Course of therapy, as referred to herein, comprises one or more separate administrations of a therapeutic agent. A course of therapy can comprise one or more cycles of a therapeutic agent.

A cycle, as used herein in the context of a cycle of administration of a drug, refers to a period of time for which a drug is administered to a patient. For example, if a drug is administered for a cycle of 21 days, the periodic administration, e.g., daily or twice daily, is given for 21 days. A drug can be administered for more than one cycle. In some embodiments, a first and second or subsequent cycle are the same in terms of one or both of duration and periodic administration. In embodiments, a first and second or subsequent cycle differ in terms of one or both of duration and periodic administration. Rest periods may be interposed between cycles. A rest cycle may be 1, 2, 4, 6, 8, 10, 12, 16, 20, 24 hours, 1, 2, 3, 4, 5, 6, 7 days, or 1, 2, 3, 4 or more weeks in length.

Numerous ranges, e.g., ranges for the amount of a drug administered per day, are provided herein. In some embodiments, the range includes both endpoints. In other embodiments, the range excludes one or both endpoints. By way of example, the range can exclude the lower endpoint. Thus, in such an embodiment, a range of 250 to 400 mg/day, excluding the lower endpoint, would cover an amount greater than 250 that is less than or equal to 400 mg/day.

As used herein, the term "subject" is intended to include human and non-human animals. In some embodiments, the subject is a human. Exemplary human subjects include a human subject having a disease or disorder described herein (e.g., abnormal cell growth, e.g., cancer (e.g., a cancer described herein)) or is suffering from a disease or disorder described herein (e.g., abnormal cell growth, e.g., cancer (e.g., a cancer described herein)). The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

EXAMPLES

The disclosure is further described in the following examples, which do not limit the scope of the claims.

Figures 1A, 1B:
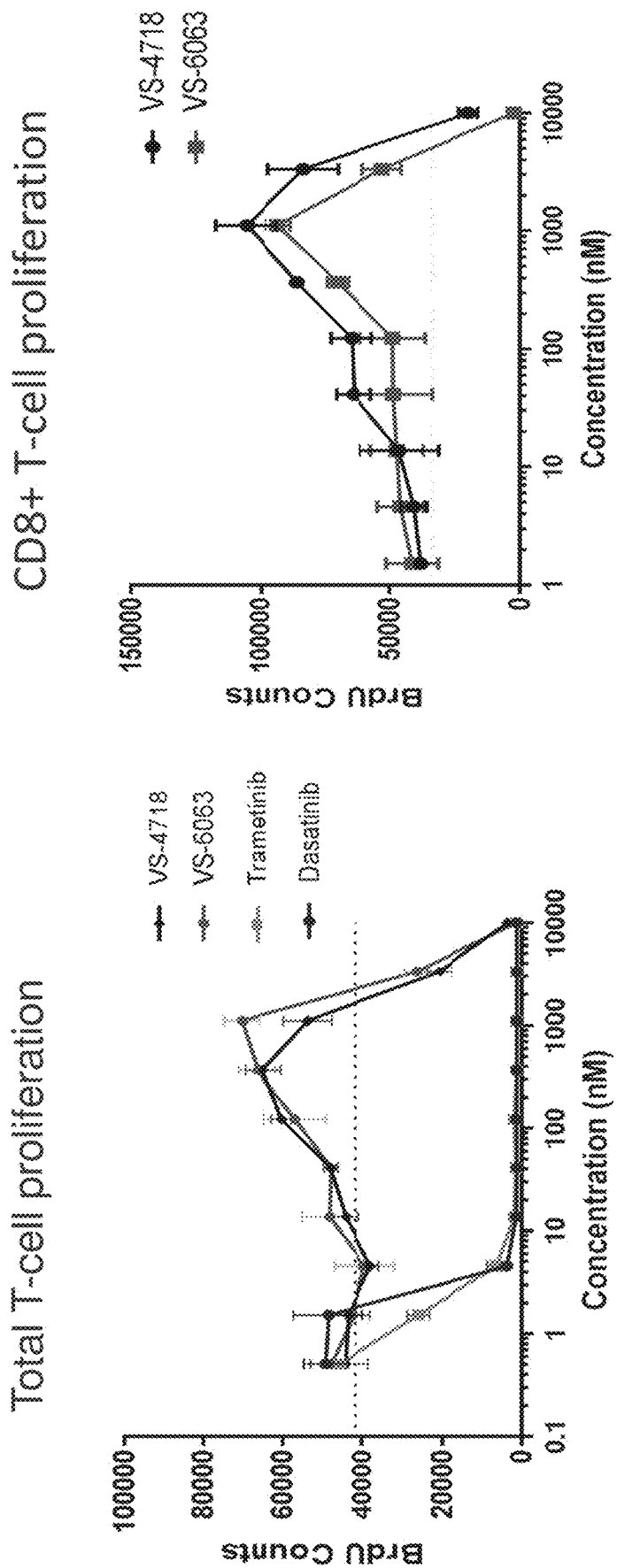
FIGS. 1A-1B show an exemplary effect of FAK Inhibitors as compared to other Tyrosine Kinase Inhibitors on T-cell proliferation.

Example 1. FAK/PYK2 Inhibition Enhances Efficacy of Immune Checkpoint Inhibition The small molecule FAK/PYK2 inhibitor VS-6063 is shown to inhibit monocyte-derived macrophages, decreases IL-6 and IL-8 production from macrophages in vitro, and reduces tumor-associated macrophages in xenograft models. Additionally, in contrast to other protein kinase inhibitors, such as the SRC inhibitor dasatinib and the MEK inhibitor trametinib which potently impair the proliferation of CD8+ cytotoxic T-cells, VS-4718 and VS-6063 stimulate proliferation of CD8+ cytotoxic T-cells (FIG. 1). Primary human CD8+ T-cells isolated from healthy donor PBMCs were incubated in the presence of anti-$CD^3$/anti-CD28 coated beads with increasing concentrations of VS-4718 or VS-6063 for 72-hours and assayed for BrdU incorporation as a measure of new DNA synthesis. Both FAK inhibitors dose-dependently increased CD8+ T-cell proliferation.

Figure 2:
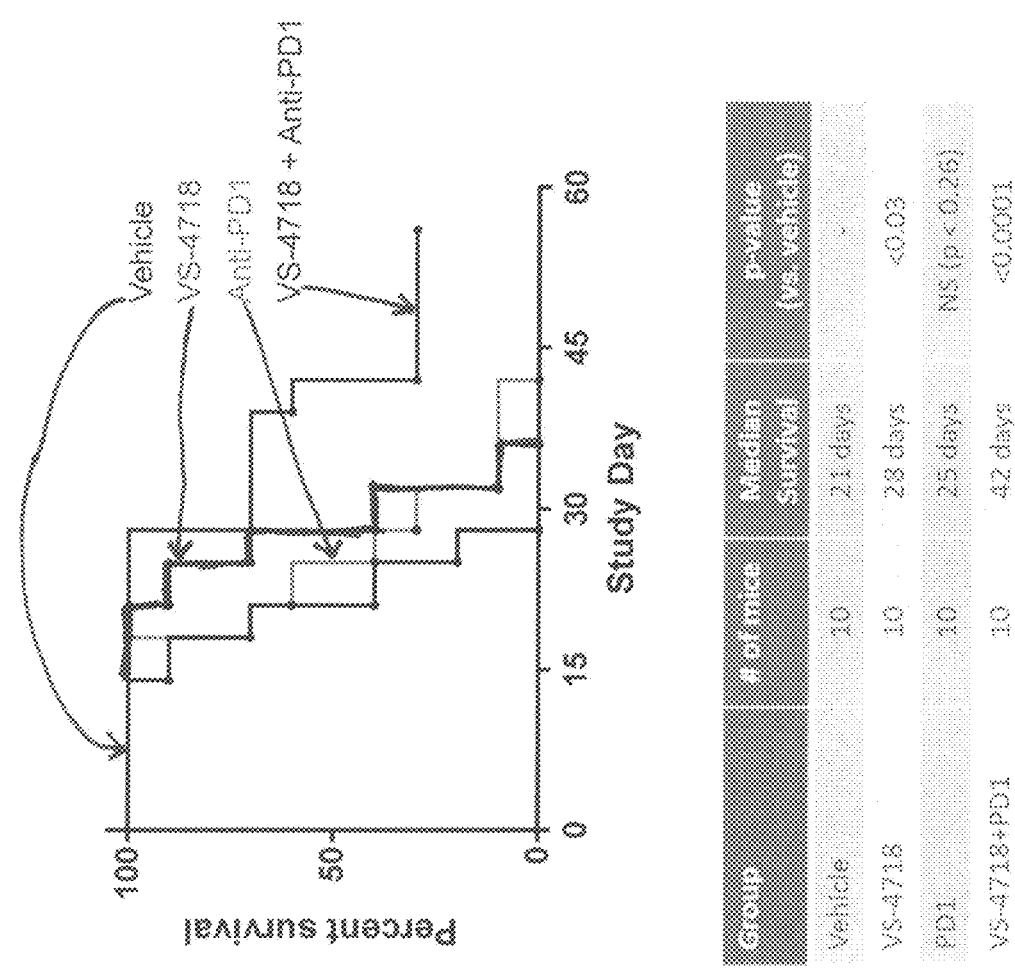
FIG. 2 shows an exemplary effect of FAK Inhibitor VS-4718 alone and in combination with anti-PD-1 on the survival of a colorectal cancer model.

Based on the inhibition of tumor-associated macrophages and enhancement of CD8+ T-cells, potentiation of FAK/PYK2 inhibitors on the anti-tumor efficacy of an anti-PD-1 monoclonal antibody in syngeneic mouse tumor models was investigated. Mice bearing established syngeneic MC38 colorectal tumors were treated with VS-4718 for 5 days before combination treatment with anti-PD1 antibody along with continued VS-4718 administration. Combination of VS-4718 with anti-PD1 extended the median overall survival to 42 days relative to 21, 25 and 28 day median overall survival with vehicle control, single agent anti-PD-1 and single agent VS-4718, respectively (FIG. 2). Moreover, on day 56, 30% of mice treated with the VS-4718/anti-PD-1 combination were still surviving compared to no surviving mice in the vehicle, single agent VS-4718 and single agent anti-PD-1 groups.

FAK kinase inhibitor or FAK genetic ablation each induced full tumor regression in a Squamous cell carcinoma model through an immune mechanism, suggested by an increase in CD8+ and CD4+ T-cells, and a decrease in T-regs.

The general pattern of immune cell changes in response to FAK inhibitors emerged across syngeneic models of skin, pancreatic, lung, and breast cancers. Increased cytotoxic T-cells were observed in tumor (for example, the CD8+ T-cell population). A decrease in immune cell populations that suppress anti-tumor immune response (for example, T-regs, M2 tumor-associated macrophages, MDSCs) was also observed. A pattern of an increase in PDL1-High tumor cells and an increase in PD-1 and cytotoxic T-cells was also seen. The data suggests synergy between FAK inhibitors and immune checkpoint antibodies (anti-PD-1 anti-CTLA-4) in multiple tumor models.

Figure 3A:
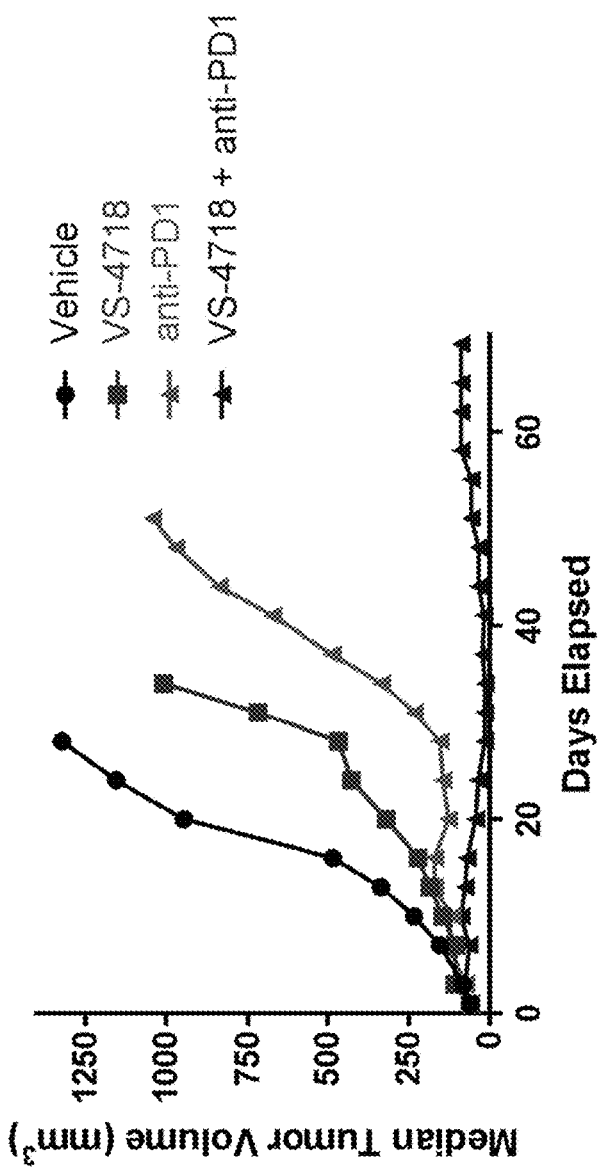
FIGS. 3A-3D show an exemplary effect of blockers of the immune checkpoint pathway and correlation with biomarkers of the immune response.

Example 2. Efficacy of FAK Inhibitors with Anti-PD-1 and Correlation with Biomarkers Mice bearing syngeneic MC38 tumors were randomized once tumors reached 50-100 mm$^3$ and treated with either vehicle, VS-4718 (75 mg/kg, BID, p.o. through end of experiment), anti-PD1 (clone RMP1-14, 10 mg/kg i.p. on days 1, 4, 8, 11) or VS-4718+anti-PD1. Median tumor volume over the days elapsed is shown in FIG. 3A. The combination of VS-4718 and anti-PD1 improved anti-tumor efficacy in syngeneic MC38 colorectal tumor-bearing mice.

Figure 3D:
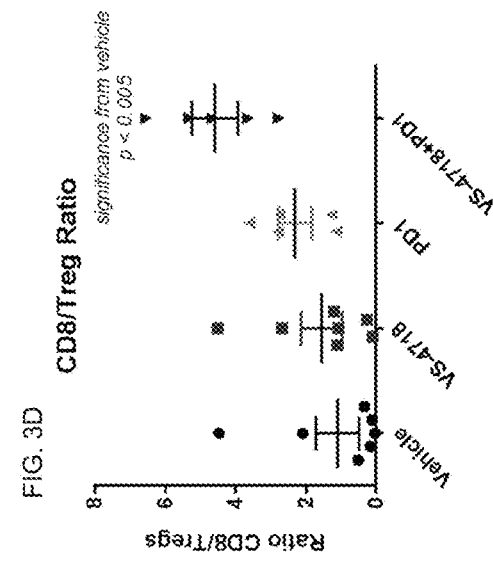
Figure 3C:
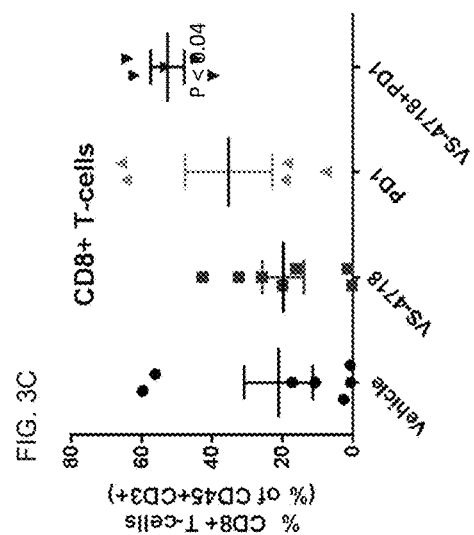
Figure 3B:
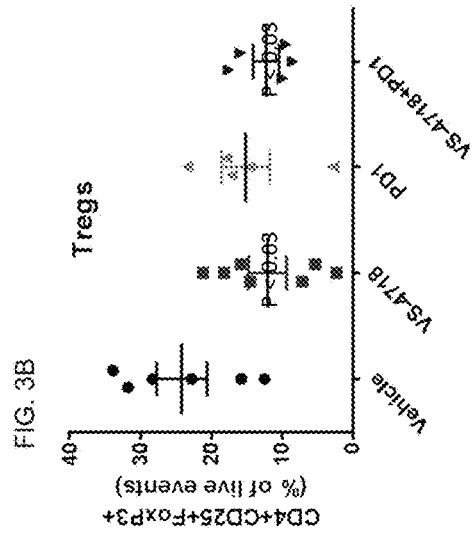

Syngeneic MC38 tumors were randomized once tumors reached 50-100 mm$^3$ and then treated with either vehicle, VS-4718 (50 mg/kg, BID), anti-PD1 (clone RMP1-14, 5 mg/kg on days 1, 4, 8, 11) or VS-4718+anti-PD1 for 12 days at which point tumors were processed live for flow cytometry (FIG. 3B-D). VS-4718 and anti-PD1 combination in MC38 tumors decreased Tregs and increased CD8+ T cells.

Figure 4:
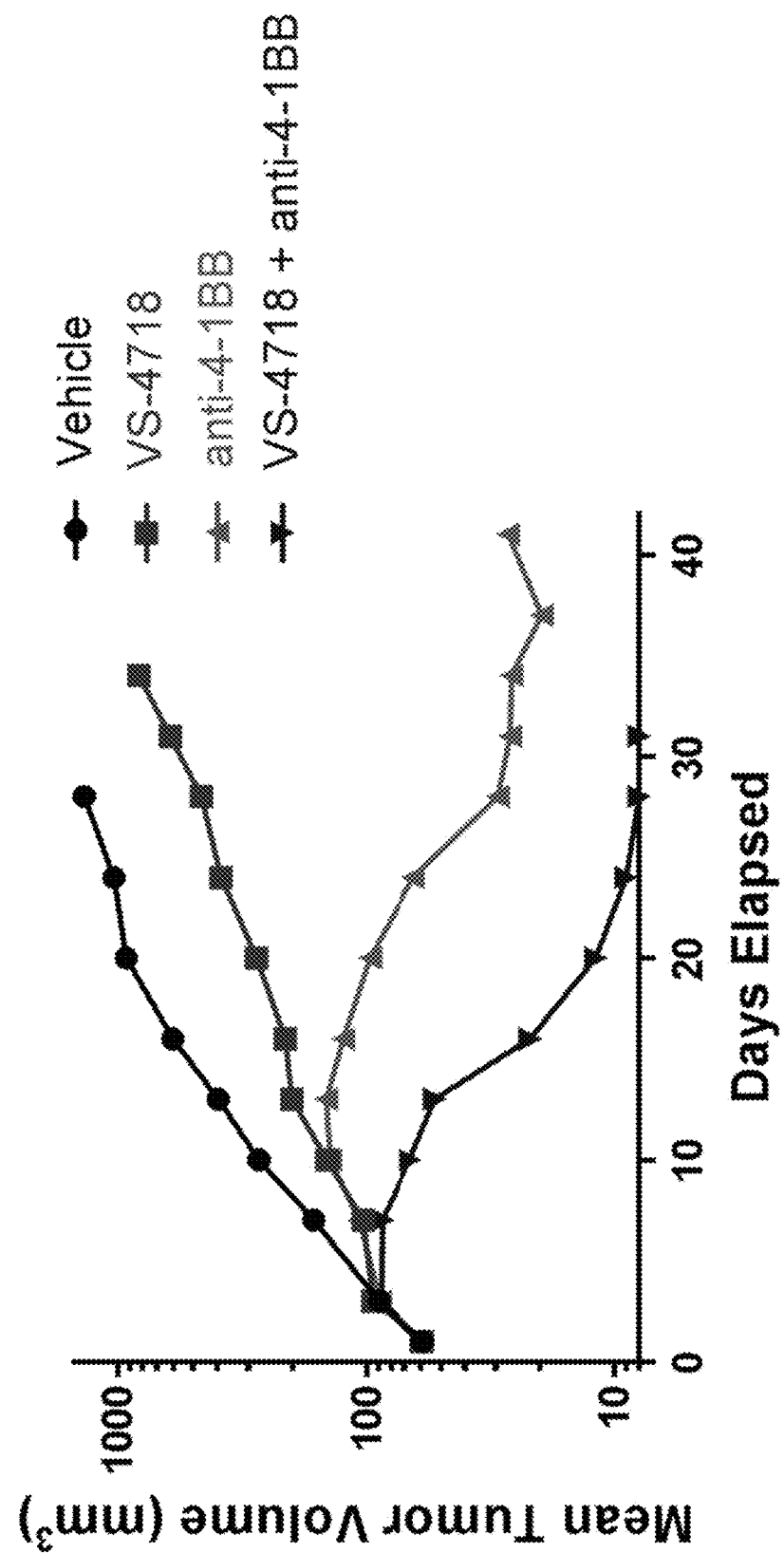
FIG. 4 shows an exemplary enhancement of anti-tumor efficacy of co-stimulatory antibodies by FAK inhibitors.

Syngeneic MC38 tumors were randomized once tumors reached 50-100 mm$^3$ and then treated with either vehicle, VS-4718 (75 mg/kg, BID, po), anti-4-1BB (clone LOB12.3, 10 mg/kg i.p. on days 1, 4, 8, 11) or VS-4718+anti-4-1BB. Mean tumor volume is plotted over time in FIG. 4. The combination of VS-4718 and anti-4-1BB improves anti-tumor efficacy in syngeneic MC38 colorectal tumor-bearing mice.

Figure 5:
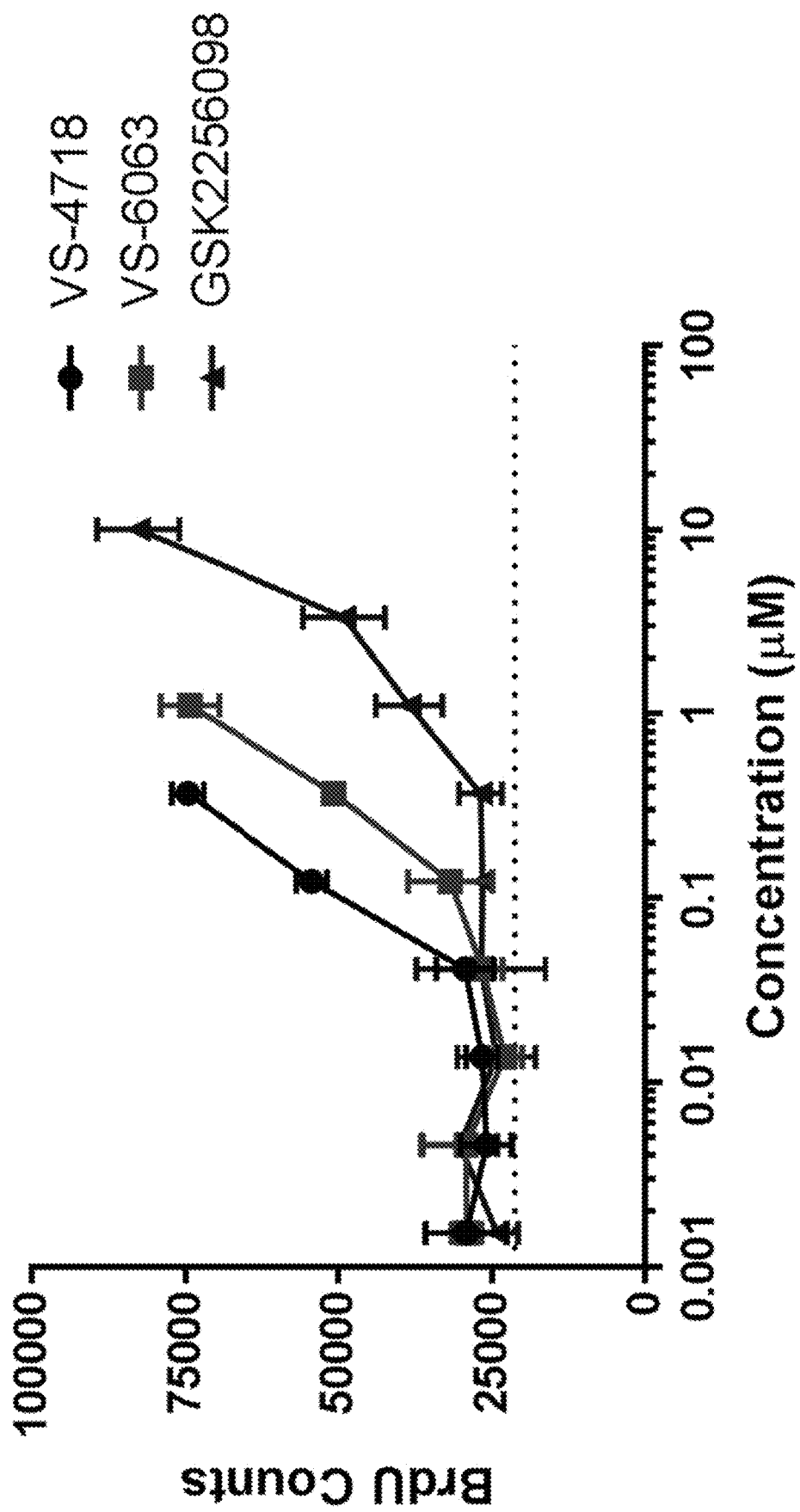
FIG. 5 shows an exemplary effect of FAK inhibitors on CD8+ T cells.

CD8+ T cells were isolated from fresh, healthy human PBMCs by negative immunomagnetic bead separation. Purified CD8+ T cells were plated on CD3-coated plates in the presence or absence of VS-4718, VS-6063, or GSK2256098 for 72 hours. Assay wells were pulsed with BrdU for the last 3-4 hours of culture and subjected to a BrdU-incorporation assay for the determination of actively proliferating cells. Data shown in FIG. 5 are presented as fold-change vs. DMSO control wells.

Figure 6B:
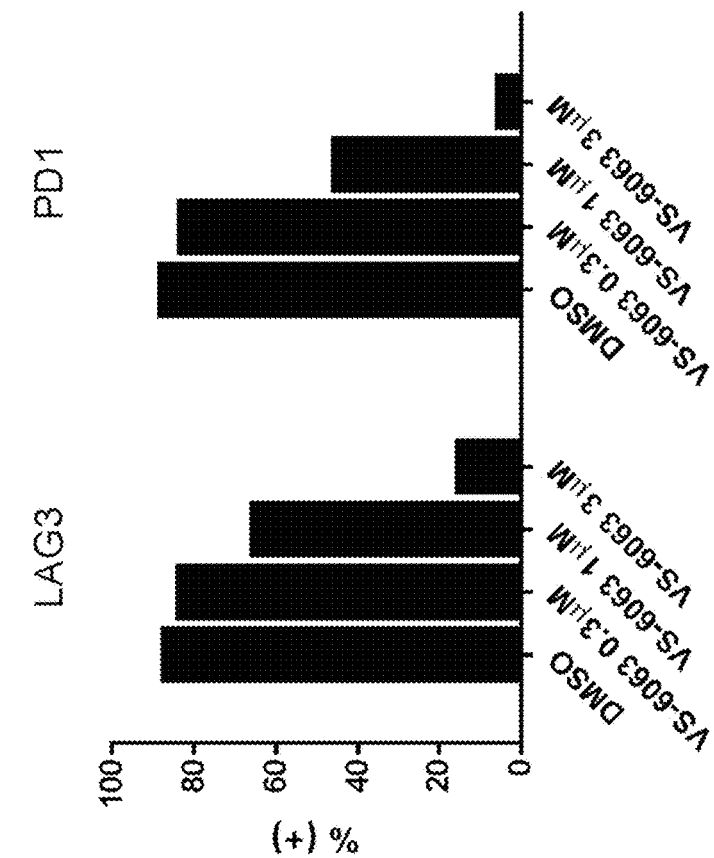
FIGS. 6A-6B show exemplary effect of FAK inhibitors on T cell exhaustion markers.
Figure 6A:
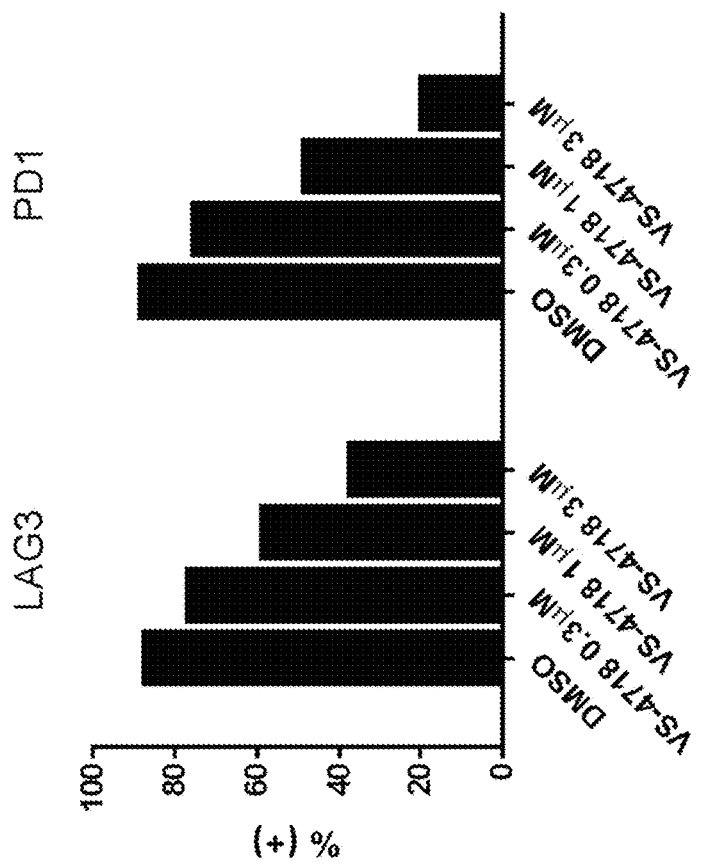

CD8+ T cells isolated from fresh, healthy human PBMCs by negative immunomagnetic bead separation were plated on anti-CD3 coated plates in the presence of VS-4718 (FIG. 6A) or VS-6063 (FIG. 6B) for 72 hours and then harvested and stained with anti-LAG3 or anti-PD-1 for flow cytometric analysis.

FAK inhibitors change the tumor immune balance to potentiate efficacy of various immuno-oncology agents. FAK inhibitor combination substantially enhances anti-tumor efficacy of anti-PD-1 or anti-4-1BB vs. each immuno-oncology antibody alone. FAK inhibitor+anti-PD-1 combination decreases Tregs and increases CD8+ T cells in MC38 tumors. FAK inhibitors increase CD8+ T cell proliferation, decrease CD8+ T cell exhaustion markers, and increase T cell-mediated tumor cell killing in vitro.

The invention claimed is:

1. A method for treating a human subject suffering from cancer, comprising administering an effective amount of a FAK inhibitor selected from VS-6063 and VS-4718, or a pharmaceutically acceptable salt thereof, in combination with an anti-PD-1 antibody, wherein the cancer is selected from the group consisting of mesothelioma, neurofibromatosis, renal cancer, lung cancer, non-small cell lung cancer, liver cancer, thyroid cancer, ovarian cancer, breast cancer, schwannoma, meningioma, schwannomatosis, acoustic neuroma, adenoid cystic carcinoma, ependymoma, and ependymal tumors.

2. The method of claim 1, wherein the cancer is solid tumor.

3. The method of claim 1, wherein the FAK inhibitor is administered orally.

4. The method of claim 3, wherein the FAK inhibitor is administered at about 100 mg to about 2000 mg.

5. The method of claim 3, wherein the FAK inhibitor is VS-6063 and the FAK inhibitor is administered at about 200 mg to about 600 mg twice a day.

6. The method of claim 3, wherein the FAK inhibitor is VS-4718 and the FAK inhibitor is administered at about 300 mg to about 500 mg once a day.

7. The method of claim 6, wherein the FAK inhibitor is VS-4718 and the FAK inhibitor is administered at about 200 mg to about 400 mg twice a day.

8. The method of claim 1, wherein the anti-PD-1 antibody is administered parenterally.

9. The method of claim 8, wherein the anti-PD-1 antibody is selected from the group consisting of: nivolumab, AMP-224, pembrolizumab, and pidilizumab.

10. The method of claim 1, wherein the subject has been previously treated with a chemotherapeutic agent or with radiation therapy.

11. The method of claim 1, wherein the subject has failed conventional or standard cancer treatment.

12. The method of claim 1, wherein the subject has failed first-line treatment.

13. The method of claim 1, wherein the anti-PD-1 antibody is nivolumab.

14. The method of claim 1, wherein the anti-PD-1 antibody is pembrolizumab.

15. The method of claim 1, wherein the anti-PD-1 antibody is AMP-224.

16. The method of claim 1, wherein the anti-PD-1 antibody is pidilizumab.

17. The method of claim 1, wherein the cancer is non-small cell lung cancer.

18. The method of claim 1, wherein the cancer is ovarian cancer.

* * * * *